United States Patent [19]

Ives

[11] Patent Number: 5,131,532
[45] Date of Patent: Jul. 21, 1992

[54] CONTACT LENS CASE

[75] Inventor: Ray C. Ives, Dallas, Tex.

[73] Assignee: Ives Ideas, Inc., Dallas, Tex.

[21] Appl. No.: 670,575

[22] Filed: Mar. 18, 1991

[51] Int. Cl.$^5$ .................. B65D 81/22; B65D 85/38
[52] U.S. Cl. ............................ 206/5.100; 206/210; 422/300
[58] Field of Search .............. 206/5, 5.1, 205, 210, 206/561, 564; 422/300, 301, 310

[56] References Cited

U.S. PATENT DOCUMENTS

| | | | |
|---|---|---|---|
| 2,944,661 | 7/1960 | Goldstein | 206/5.1 |
| 3,168,100 | 2/1965 | Rich | 206/5.1 |
| 3,279,482 | 10/1966 | Hungerford et al. | 206/5.1 |
| 3,314,533 | 4/1987 | Kopfle | 206/5.1 |
| 3,536,082 | 10/1970 | Kolbeck | 206/5.1 |
| 4,337,858 | 7/1982 | Thomas et al. | 206/5.1 |

Primary Examiner—Jimmy G. Foster
Attorney, Agent, or Firm—Timmons & Kelly

[57] ABSTRACT

A contact lens case having a container for liquid solution, a tray which fits into the container and having a substantially flat portion for the contact lens to rest on and an annular beveled outer portion for retarding the outward movement of the lens. A dividing perpendicular bar extending upwardly from the top of the tray and serves both to separate the right lens from the left lens and to act as a handle for lifting the tray. The tray forms apertures adjacent to or in rear proximity to the bar and other apertures to form the letter "L" on one side of the bar and the letter "R" on the other side. A removable cap forms ridges on its inside to prevent the creation of suction between it and the concave side of a lens.

28 Claims, 2 Drawing Sheets ic Field

The present invention relates generally to the storage and cleaning of contact lens, and in particular, to contact lens cases.

During soaking, disinfecting, or neutralizing, contact lens are usually contained within a small case, along with an appropriate liquid solution. After a given amount of time, the contact lens must be carefully removed from the case. The lens are fragile and can be easily damaged.

2. Background Art

In most contact lens cases, the lens must be fished out of the solution with a finger or some form of tweezers. The lens can be easily scratched or oil from the finger can get on the lens. Handling the lens gives increased opportunity for contamination and damage.

U.S. Pat. No. 2,944,661 issued to Goldstein shows the use of a removable basket with a long "agitator arm" used for moving the contact lens through the solution and agitating the solution around the lens.

U.S. Pat. No. 3,168,100 issued to Rich shows a container with a tray having a peripheral upstanding wall and apertures spread throughout. A cover is used to keep the lens in place. The lens must still be fished out because of the peripheral wall which prevents access to the edges of the lens.

U.S. Pat. No. 3,536,082 issued to Kolbeck shows a case with a removable tray. The tray forms deep pockets or compartments with apertures formed at the bottom of those pockets or compartments for ensuring that the lens are pulled to the bottom of the pockets as the tray is removed. The lens thus do not float off of the tray or get mixed up, but they are even more difficult to remove.

DISCLOSURE OF THE INVENTION

In accordance with the present invention, a contact lens case for containing a pair of contact lens in a liquid solution includes both a container for the solution and a tray for holding the lens in the solution. The container forms a bottom and a substantially upright wall. The top surface of the tray includes a substantially flat circular inner portion for the contact lens to rest on and an annular beveled outer portion for retarding the outward movement of the contact lens.

A divider, in a preferred form a dividing perpendicular bar which also serves as a handle, extending from the top surface of the tray, separates the top of the tray into roughly equal sections. Each section is larger than one contact lens of the pair. The tray forms a plurality of apertures from top to bottom on each side of and adjacent to or in near proximity to the divider. Most of the liquid solution flows through these apertures when the tray is being lifted out of the solution. The height of the dividing perpendicular bar is less than one third of either length or diameter of the top of the tray and serves as a handle for lifting the tray. Because of the room left on the flat portion of the top surface which is adjacent to a lens because of the semicircular shape, a user has easy access to opposite positions of the lens edge. A support member is formed on the inside of the upright wall for supporting the tray in a position where the tray does not touch the bottom of the container.

In one arrangement, the tray forms at least one aperture from top to bottom on one side of the divider forming the letter "L" and at least one aperture from top to bottom on the other side of the divider forming the letter "R".

A removable cap screws onto the container to prevent spillage of the liquid and lens. In one arrangement, the inside of the cap forms a series of ridges to prevent the creation of suction between the inside of the cap and the lens.

These and other objects, advantages and features of this invention will be apparent from the following description taken with reference to the accompanying drawing, wherein is shown the preferred embodiments of the invention.

BEST MODE FOR CARRYING OUT THE INVENTION

Figure 1:
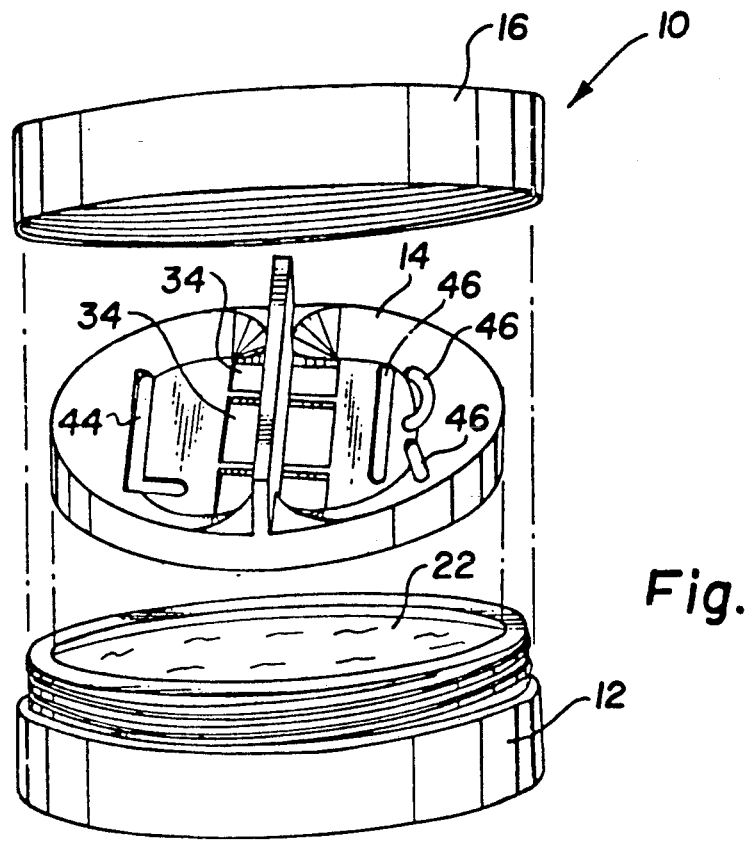
FIG. 1 is an exploded view of a contact lens case according to the present invention showing liquid solution.
Figure 2:
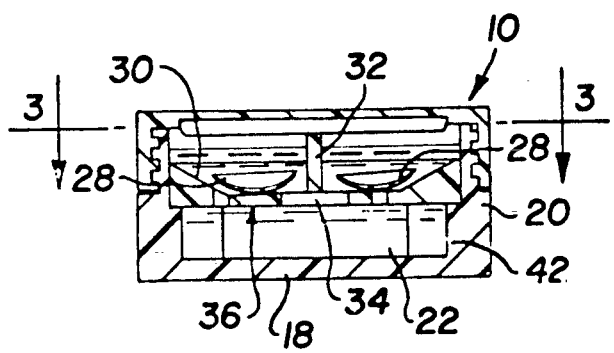
FIG. 2 is a sectional elevational view thereof at a smaller scale, showing contact lens in section and liquid solution.

Referring now to the drawing, and in particular to FIG. 1, a contact lens case according to the present invention is referred to generally by reference numeral 10. Case 10 includes a container 12, a tray 14 and a removable cap 16. Referring also to FIG. 2, container 12 includes both a bottom 18 and a substantially upright wall 20 for containing a quantity of liquid solution 22. Tray 14 is designed to loosely fit within upright wall 20 for easy removal. Top surface 24 of tray 14 includes a substantially flat circular inner portion 26 for contact lens 28 to rest on and an annular beveled outer portion 30 for retarding outward movement of contact lens 28.

Figure 3:
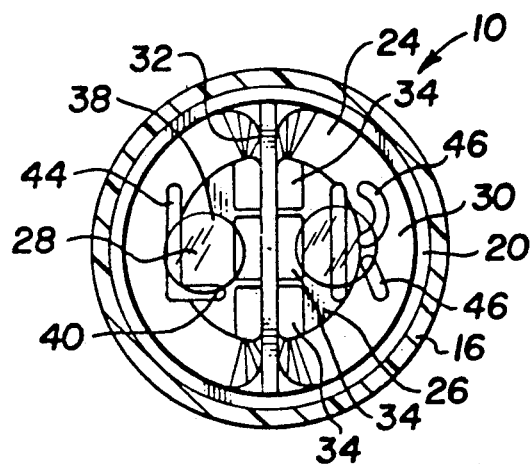
FIG. 3 is a sectional view thereof taken at 3—3 of FIG. 2.

Referring now also to FIG. 3, a divider such as a dividing perpendicular bar 32 extends from top surface 24, separating the top of the tray into roughly equal sections, each section slightly larger than one contact lens 28. Tray 14 forms a plurality of apertures 34 from top surface 24 through to bottom surface 36 on each side of and adjacent to or in near proximity to dividing perpendicular bar 32. Most of liquid solution 22 flows through apertures 34 when tray 14 is lifted out of the solution, pulling lens 28 toward the center of the tray rather than washing or floating it over the side. Tray 12 also forms at least one aperture 44 from top to bottom on one side of dividing perpendicular bar 32 forming the letter "L" and at least one aperture 46 from top to bottom on the other side of the dividing perpendicular bar forming the letter "R". The large letters "R" and "L" formed by apertures are easily seen and can even be distinguished by feel in the dark. Apertures 44 and 46 also help drain tray 12 as it is lifted from the solution, but most of the drainage is still from apertures 34 near the dividing bar.

Dividing perpendicular bar 32 also acts as a handle for lifting the tray. The height of dividing bar 32, being the distance from its base at top surface 14 to the point on the bar which is the greatest perpendicular distance away from the top surface, is less than one third of its length of the diameter of the tray. This allows the lens to only be a certain distance under the fluid, reducing the chance of spilling from taking the lens out of the solution and reducing the chance of floating the lens off the tray. Because of the semicircular shape of each tray half formed by dividing bar 32, a user has easy access to opposite portions 38 and 40 of the lens edge when the lens is resting convex side down on the tray top and the tray is removed from the container.

Contact lens case 10 also includes a support member 42 for keeping bottom surface 36 of tray 14 from resting on the bottom 18 of container 12. This allows the keeping of the required amount of solution in the case and essentially keeping lens 28 in the middle of the solution. It also makes it easier to remove tray 14.

Figure 5:
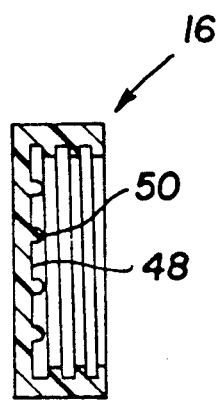
FIG. 5 is a sectional view thereof taken at 5—5 of FIG. 4.
Figure 4:
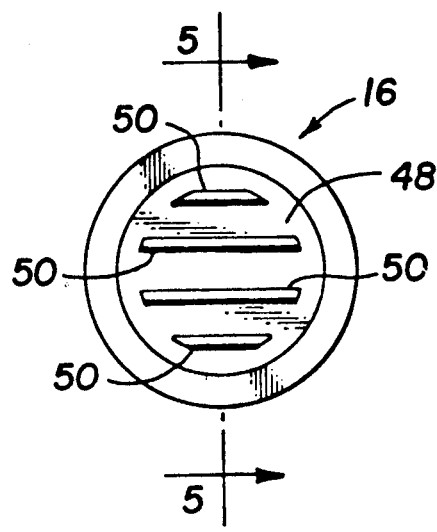
FIG. 4 is a bottom view of a cap of a contact lens case according to the present invention.

Referring now to FIG. 4 and FIG. 5, inside 48 of removable cap 16 forms ridges 50 to prevent the creation of suction between the inside of the cap and the concave side of the lens should the case be turned upside down or sideways during travel.

From the foregoing it will be seen that this invention is one well adapted to attain all of the ends and objects hereinabove set forth, together with other advantages which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the figures of the accompanying drawing is to be interpreted as illustrative and not in a limiting sense.

I claim:

1. A contact lens case for containing a pair of contact lens in a liquid solution, comprising in combination:
   a container forming a substantially circular bottom and a substantially upright wall for containing a quantity of the liquid solution;
   a substantially circular tray comprising a top and a bottom, designed to fit into the container, loosely fitting within the upright wall for easy removal;
   a dividing perpendicular bar extending from the top of the tray and separating the top of the tray into roughly equal substantially semicircular sections, each section forming a substantially semicircular flat top surface surrounded by a substantially semicircular inwardly beveled outer portion for retarding outward movement of the contact lens, each section slightly larger than one contact lens of the pair wherein the tray forms an aperture from top to bottom on each side of and substantially immediately adjacent to the dividing perpendicular bar, allowing most of the liquid solution to flow through said aperture when the tray is being lifted out of the solution, whereby the dividing perpendicular bar can serve as a handle and wherein the top surface on each side of the dividing bar is large enough for the contact lens to move transversely to said dividing bar and along said flat surface when that lens is resting convex side down on the top of the tray and the tray is removed from the container.

2. A contact lens case according to claim 1 wherein the substantially upright wall forms an inner surface and an outer surface, the case further including a support member integral with the inner surface of the substantially upright wall to support the tray wherein the tray does not rest on the bottom of the container and wherein the height of the dividing perpendicular bar is less than one third of the diameter of the top of the tray.

3. A contact lens case according to claim 2 wherein the tray forms at least one aperture from top to bottom on one side of the dividing perpendicular bar forming the letter "L" and at least one aperture from top to bottom on the other side of the dividing perpendicular bar forming the letter "R".

4. A contact lens case according to claim 3 further including a removable cap to securely fasten to the container for retaining the lens and solution within the container wherein the inside of the cap forms ridges to prevent the creation of suction between the inside of the cap and the lens.

5. A contact lens case according to claim 1 wherein the tray forms at least one aperture from top to bottom on one side of the dividing perpendicular bar forming the letter "L" and at least one aperture from top to bottom on the other side of the dividing perpendicular bar forming the letter "R".

6. A contact lens case according to claim 5 further including a removable cap to securely fasten to the container for retaining the lens and solution within the container wherein the inside of the cap forms ridges whereby a contact lens will not form a suction pocket with the inside of the cap.

7. A contact lens case according to claim 1 further including a removable cap to securely fasten to the container for retaining the lens and solution within the container wherein the inside of the cap forms ridges whereby a contact lens will not form a suction pocket with the inside of the cap.

8. A contact lens case for containing a pair of contact lens in a liquid solution, comprising in combination:
   a container forming a substantially circular bottom and a substantially upright wall for containing a quantity of the liquid solution;
   a substantially circular tray comprising a top and a bottom designed to fit into the container, loosely fitting within the upright wall for easy removal,
   a divider affixed to the top of the tray and separating the top of the tray into roughly equal substantially semicircular sections, each section forming a substantially semicircular flat top surface surrounded by a substantially semicircular inwardly beveled outer portion for retarding outward movement of the contact lens, each section slightly larger than one contact lens of the pair wherein the tray forms an aperture from top to bottom on each side of and substantially immediately adjacent to the divider, allowing most of the liquid solution to flow through said aperture when the tray is being lifted out of the solution and wherein the top surface on each side of the divider is large enough for the contact lens to move transversely to said divider and along said flat top surface when that lens is resting convex side down on the top of the tray and the tray is removed from the container.

9. A contact lens case according to claim 8 wherein the substantially upright wall forms an inner surface and an outer surface, the case further including a support member integral with the inner surface of the substantially upright wall to support the tray wherein the tray does not rest on the bottom of the container.

10. A contact lens case according to claim 9 wherein the tray forms at least one aperture from top to bottom on one side of the divider forming the letter "L" and at least one aperture from top to bottom on the other side of the divider forming the letter "R".

11. A contact lens case according to claim 10 further including a removable cap to securely fasten to the container for retaining the lens and solution within the container wherein the inside of the cap forms ridges whereby a contact lens will not form a suction pocket with the inside of the cap.

12. A contact lens case according to claim 8 wherein the tray forms at least one aperture from top to bottom on one side of the divider forming the letter "L" and at least one aperture from top to bottom on the other side of the divider forming the letter "R".

13. A contact lens case according to claim 12 further including a removable cap to securely fasten to the container for retaining the lens and solution within the container wherein the inside of the cap forms ridges whereby a contact lens will not form a suction pocket with the inside of the cap.

14. A contact lens case according to claim 8 further including a removable cap to securely fasten to the container for retaining the lens and solution within the container wherein the inside of the cap forms ridges whereby a contact lens will not form a suction pocket with the inside of the cap.

15. A tray for holding a pair of contact lens while being lifted from a liquid, comprising:
   a substantially circular top which forms a substantially flat inner portion for the contact lens to rest on and an inwardly beveled outer portion for retarding outward movement of the contact lens;
   a bottom; and
   a dividing perpendicular bar extending from the top surface of the tray and separating the top of the tray into roughly equal substantially semicircular sections, each section forming a substantially semicircular flat top surface surrounded by a substantially semicircular inwardly beveled outer portion for retarding outward movement of the contact lens, each section slightly larger than one contact lens of the pair wherein the tray forms an aperture from the flat portion of the top surface to the bottom of the tray on each side of and substantially immediately adjacent to the dividing perpendicular bar, allowing most of the liquid to flow through said aperture when the tray is being lifted out of the liquid, whereby the dividing perpendicular bar can serve as a handle and wherein the top surface on each side of the dividing bar is large enough for the contact lens to move transversely to said dividing bar and along said flat top surface when that lens is resting convex side down on the top surface of the tray and the tray is exposed.

16. A tray according to claim 15 wherein the tray also forms at least one aperture from top to bottom on one side of the dividing perpendicular bar forming the letter "L" and at least one aperture from top to bottom on the other side of the dividing perpendicular bar forming the letter "R".

17. A tray according to claim 15 wherein the height of the dividing perpendicular bar is less than one third of the diameter of the top of the tray.

18. A contact lens case for containing a pair of contact lens in a liquid solution, comprising in combination:
   a container forming a bottom and a substantially upright wall for containing a quantity of the liquid solution;
   a tray comprising a top and a bottom, designed to fit into the container, loosely fitting within the upright wall for easy removal, wherein the top surface of the tray forms a substantially flat inner portion for the contact lens to rest on and an inwardly beveled outer portion for retarding outward movement of the contact lens;
   a dividing perpendicular bar extending from the top of the tray and separating the top of the tray into roughly equal sections, each section slightly larger than one contact lens of the pair wherein the tray forms at least one aperture from top to bottom on one side of the dividing perpendicular bar forming the letter "L" and at least one aperture from top to bottom on the other side of the dividing perpendicular bar forming the letter "R", whereby the dividing perpendicular bar can serve as a handle and wherein the substantially flat inner portion on each side of the dividing bar is large enough for a user to have access to opposite positions of the edge of one of the lens when that lens is resting convex side down on the top of the tray and the tray is removed from the container.

19. A contact lens case according to claim 18 wherein the substantially upright wall forms an inner surface and an outer surface, the case further including a support member integral with the inner surface of the substantially upright wall to support the tray wherein the tray does not rest on the bottom of the container and wherein the height of the dividing perpendicular bar is less than one third of the diameter of the top of the tray.

20. A contact lens case according to claim 19 further including a removable cap to securely fasten to the container for retaining the lens and solution within the container wherein the inside of the cap forms ridges to prevent the creation of suction between the inside of the cap and the lens.

21. A contact lens case according to claim 18 further including a removable cap to securely fasten to the container for retaining the lens and solution within the container wherein the inside of the cap forms ridges whereby a contact lens will not form a suction pocket with the inside of the cap.

22. A contact lens case for containing a pair of contact lens in a liquid solution, comprising in combination:
   a container forming a bottom and a substantially upright wall for containing a quantity of the liquid solution;
   a tray comprising a top and a bottom designed to fit into the container, loosely fitting within the upright wall for easy removal, wherein the top surface of the tray forms a substantially flat circular inner portion for the contact lens to rest on and an annular inwardly beveled outer portion for retarding outward movement of the contact lens;
   a divider affixed to the top of the tray and separating the top of the tray into roughly equal sections, each section slightly larger than one contact lens of the pair wherein the tray forms at least one aperture from top to bottom on one side of the divider forming the letter "L" and at least one aperture from top to bottom on the other side of the divider forming the letter "R" and wherein the substantially flat inner portion on each side of the divider is large enough for a user to have access to opposite positions of the edge of one of the lens when that lens is resting convex side down on the top of the tray and the tray is removed from the container.

23. A contact lens case according to claim 22 wherein the substantially upright wall forms an inner surface and an outer surface, the case further including a support member integral with the inner surface of the substantially upright wall to support the tray wherein the tray does not rest on the bottom of the container.

24. A contact lens case according to claim 23 further including a removable cap to securely fasten to the container for retaining the lens and solution within the container wherein the inside of the cap forms ridges whereby a contact lens will not form a suction pocket with the inside of the cap.

25. A contact lens case according to claim 22 further including a removable cap to securely fasten to the container for retaining the lens and solution within the container wherein the inside of the cap forms ridges whereby a contact lens will not form a suction pocket with the inside of the cap.

26. A tray for holding a pair of contact lens while being lifted from a liquid, comprising:
   a top which forms a substantially flat inner portion for the contact lens to rest on and an inwardly beveled outer portion for retarding outward movement of the contact lens;
   a bottom; and
   a dividing perpendicular bar extending from the top surface of the tray and separating the top of the tray into roughly equal sections, each section slightly larger than one contact lens of the pair wherein the tray forms at least one aperture from top to bottom on one side of the dividing perpendicular bar forming the letter "L" and at least one aperture from top to bottom on the other side of the dividing perpendicular bar forming the letter "R", whereby the dividing perpendicular bar can serve as a handle and wherein the substantially flat inner portion on each side of the dividing bar is large enough for a user to have access to opposite positions of the edge of one of the lens when that lens is resting convex side down on the top surface of the tray and the tray is exposed.

27. A tray according to claim 26 wherein the height of the dividing perpendicular bar is less than one third of either the length or the diameter of the top of the tray.

28. A tray for holding a pair of contact lens while being lifted from a liquid, comprising:
   a top which forms a substantially flat portion for the contact lens to rest on;
   a bottom; and
   wherein the tray forms at least one aperture from top to bottom forming the letter "L" and at least one aperture from top to bottom forming the letter "R", wherein the substantially flat portion is large enough for one contact lens over or near each aperture and for a user to have access to opposite positions of the edge of one of the lens when that lens is resting convex side down on the top surface of the tray and the tray is exposed.

* * * * *